United States Patent
Hamamoto et al.

(10) Patent No.: US 11,461,598 B2
(45) Date of Patent: Oct. 4, 2022

(54) INFORMATION PROCESSING DEVICE, INFORMATION PROCESSING PROGRAM, AND INFORMATION PROCESSING METHOD

(71) Applicant: Yamaguchi University, Yamaguchi (JP)

(72) Inventors: Yoshihiko Hamamoto, Yamaguchi (JP); Horiyuki Ogihara, Yamaguchi (JP); Norio Iizuka, Yamaguchi (JP); Takao Tamesa, Yamaguchi (JP); Masaaki Oka, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 1054 days.

(21) Appl. No.: 16/079,835

(22) PCT Filed: Dec. 26, 2016

(86) PCT No.: PCT/JP2016/088734
§ 371 (c)(1),
(2) Date: May 17, 2019

(87) PCT Pub. No.: WO2017/145517
PCT Pub. Date: Aug. 31, 2017

(65) Prior Publication Data
US 2021/0182630 A1    Jun. 17, 2021

(30) Foreign Application Priority Data
Feb. 26, 2016    (JP) .............................. JP2016-035605

(51) Int. Cl.
G06K 9/62       (2022.01)
G16H 50/20      (2018.01)
A61B 5/00       (2006.01)

(52) U.S. Cl.
CPC .......... *G06K 9/6277* (2013.01); *A61B 5/7267* (2013.01); *G06K 9/6234* (2013.01); *G16H 50/20* (2018.01)

(58) Field of Classification Search
CPC ... A61B 2503/42; A61B 5/7267; G06F 16/00; G06K 9/6234; G06K 9/6277;
(Continued)

(56) References Cited

U.S. PATENT DOCUMENTS 5,063,603 A * 11/1991 Burt .................. G06V 30/2504
                                                     382/226
7,783,082 B2 * 8/2010 Koshizen ............. G06V 40/171
                                                     382/116

(Continued)

FOREIGN PATENT DOCUMENTS

| JP | 2013-524865 A | 6/2013 |
| JP | 2013-532295 A | 8/2013 |
| JP | 2016-210216 A | 12/2016 |

OTHER PUBLICATIONS

Tateishi R, Yoshida H, Shiina S, et al: Proposal of a New Prognostic Model for Hepatocellular Carcinoma—an Analysis of 403 Patients. Gut 54: 419-425, 2005.
(Continued)

*Primary Examiner* — Tsung Yin Tsai
(74) *Attorney, Agent, or Firm* — WCF IP

(57) ABSTRACT

An information processor can logically support prediction based on past statistical information even though the information contains qualitative or non-numerical data. The processor determines whether an input pattern corresponding to an input object (a determination target) belongs to a specific class among multiple classes, based on feature subsets of any combination of a plurality of features, each feature comprises multiple categories. The processor
(Continued)

includes a storage storing the input pattern corresponding to the input object and samples corresponding to respective sample objects and a classification determiner determining whether the input pattern belongs to the specific class. The classification determiner calculates a first conditional probability and a second conditional probability based on the number of the samples belonging to each category of the respective features, the first conditional probability is a probability that the data of the input pattern belong to categories corresponding to the respective feature for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples, and determines whether the input pattern belongs to the specific class based on the feature information on the input pattern, the first conditional probability and the second conditional probability.

28 Claims, 11 Drawing Sheets

(58) Field of Classification Search
CPC ........ G06K 9/6278; G06N 5/04; G06N 99/00; G06V 2201/03; G16H 50/20
See application file for complete search history.

(56) References Cited

U.S. PATENT DOCUMENTS

| | | | | |
|---|---|---|---|---|
| 9,589,245 | B2* | 3/2017 | Coden | G06F 21/554 |
| 2006/0280341 | A1* | 12/2006 | Koshizen | G06K 9/6255 |
| | | | | 382/118 |
| 2011/0040837 | A1* | 2/2011 | Eden | G06F 40/40 |
| | | | | 709/206 |
| 2012/0301887 | A1* | 11/2012 | Bankaitis-Davis | C12Q 1/6886 |
| | | | | 435/6.12 |
| 2014/0079297 | A1* | 3/2014 | Tadayon | G06V 40/172 |
| | | | | 382/118 |
| 2015/0286819 | A1* | 10/2015 | Coden | G06F 21/554 |
| | | | | 726/23 |

OTHER PUBLICATIONS

Ikai H, Takayasu K, Omata M, et al: A modified Japan Integrated Stage Score for Prognostic Assessment in Patients with Hepatocellular Carcinoma. J Gastroenterology, 41, 884-892, 2006.

M. Minagawa, I. Ikai, Y. Matsuyama, Y. Yamaoka, M. Makuuchi, Staging of Hepatocellular Carcinoma Assessment of the Japanese TNM and AJCC/UICC TNM Systems in a Cohort of 13,772 Patients in Japan, Annals of Surgery, vol. 245, No. 6, pp. 909-922, Jun. 2007.

JM Henderson, M. Sherman, A. Tavill, M. Abecassis, G. Chejfec, and T. Gramlich, AHPBA/AJCC Consensus Conference on Staging of Hepatocellular Carcinoma: Consensus Statement, HPB, vol. 5, No. 4, pp. 243-250, 2003.

Kamoshida et al: "MALSS: A tool to Support data Analysis using Machine Learning for Novices", IEICE Transactions on Informaiton and Systems, Dec. 14, 2015.

* cited by examiner

| Feature ID | Sample ID | | |
|---|---|---|---|
| | $D_1$ | $D_2$ | ... |
| $x_1$ | $V_{11}$ | $V_{21}$ | ... |
| $x_2$ | $V_{21}$ | $V_{22}$ | ... |
| ... | ... | ... | ... |

FIG. 2

| Sample ID | $D_1$ | $D_2$ | $D_3$ | $D_4$ | ... |
|---|---|---|---|---|---|
| Class ID | $\omega_2$ | $\omega_1$ | $\omega_1$ | $\omega_2$ | ... |

FIG. 3

| Feature ID | Category ID | Sample ID (training samples) | | |
|---|---|---|---|---|
| | | $D_{t1}$ | $D_{t2}$ | ... |
| $x_1$ | $x_{1(1)}$ | – | ○ | ... |
| | $x_{1(2)}$ | ○ | – | ... |
| $x_2$ | $x_{2(1)}$ | – | – | ... |
| | $x_{2(2)}$ | ○ | ○ | ... |
| | $x_{2(3)}$ | – | – | ... |
| ... | ... | ... | ... | ... |

FIG. 4

| Feature ID | Category ID | Class ID | |
|---|---|---|---|
| | | $\omega_1$ | $\omega_2$ |
| $x_1$ | $x_{1(1)}$ | $n^1_{1(1)}$ | $n^2_{1(1)}$ |
| | $x_{1(2)}$ | $n^1_{1(2)}$ | $n^2_{1(2)}$ |
| $x_2$ | $x_{2(1)}$ | $n^1_{2(1)}$ | $n^2_{2(1)}$ |
| | $x_{2(2)}$ | $n^1_{2(2)}$ | $n^2_{2(2)}$ |
| | $x_{2(3)}$ | $n^1_{2(3)}$ | $n^2_{2(3)}$ |
| ... | ... | ... | ... |

FIG. 5

| Feature ID | Category ID | Sample ID (test samples) | | |
|---|---|---|---|---|
| | | $D_{e1}$ | $D_{e2}$ | ... |
| $x_1$ | $x_{1(1)}$ | ( ) | ( ) | ... |
| | $x_{1(2)}$ | – | – | ... |
| $x_2$ | $x_{2(1)}$ | ( ) | – | ... |
| | $x_{2(2)}$ | – | – | ... |
| | $x_{2(3)}$ | – | ( ) | ... |
| ... | ... | ... | ... | ... |
| Class label Information | | $\omega_1$ | $\omega_2$ | ... |
| Classification Information | | $\omega_1$ | $\omega_1$ | ... |
| Judgement Information | | T | F | ... |

FIG. 8

Examination items required for prediction of recurrence of @@@ among examination items $Y_1, Y_2, Y_3 \cdots Y_n$ are listed below

| Priority | Feature subset of examination items | Posterior probability |
|---|---|---|
| 1 | $Y_1, Y_2, Y_3$ | P1 |
| 2 | $Y_1, Y_2$ | P2 |
| 3 | $Y_1, Y_3$ | P3 |
| ... | ... | ... |

FIG. 11

Adding result of examination corresponding to examination item $Z_3$ to results of examinations corresponding to examination items $Z_1$ and $Z_2$ conducted on patient can improve accuracy of prediction of recurrence of @@@

FIG. 12

INFORMATION PROCESSING DEVICE, INFORMATION PROCESSING PROGRAM, AND INFORMATION PROCESSING METHOD

TECHNICAL FIELD

The present invention relates to an information processor, a program for processing information, and a method of processing information that support predicting whether a specific event occurs among multiple events.

BACKGROUND ART

Pattern recognition is one of decision-making processes in artificial intelligence. An object to be recognized is measured and then expressed as a pattern formed by the acquired data. In pattern recognition, the pattern is assigned to a predefined class. The Bayes decision rule has been known as one of the powerful statistical classification techniques.

An example field to which pattern recognition is applied is clinical practice. That is, the clinical data of a patient to be diagnosed form a pattern, and the pattern is assigned to a class or one of diagnosis results, (whether the patient is in a specific disease state or whether a specific disease will recur in a treated patient).

A technique has been proposed for determining whether a patient is in a specific disease state using the Bayes decision rule in statistical pattern recognition (For example, refer to PTL 1). However, the clinical data of a patient used in the technique disclosed in PTL 1 only contains quantitative data, i.e., numeric data. That is, the technique in PTL 1 cannot handle qualitative data, i.e., non-numeric data.

Another technique is proposed for representing the hepatic state of a patient through a scoring system based on the clinical data of the patient including qualitative data, besides statistical pattern recognition (for example, refer to NPL 1, 2, 3, and 4). For example, TNM classification categorizes cancers of interest using T, N, and M factors. The T factor determines a score value based on "the number of sites", "size" and "vascular invasion" of the cancer; the N factor determines a score value based on "lymphatic metastasis" or "no lymphatic metastasis"; and the M factor determines a score value based on "distant metastasis" or "no distant metastasis". The sum of the score values of all the factors is calculated and compared with a predetermined cutoff value to diagnose. The N and M factors are non-numerical data (for example, "lymphatic metastasis" or "no lymphatic metastasis"). In other words, the such factors which are so-called "non-numerical variables" have no numerical meaning. Thus, the statistical information (mean, variance, for example) cannot be calculated for the factors.

In clinical practices, the refractory nature of liver cancer is due to the high probability of its recurrence, for example. That is, even if all of the cancer is completely removed by surgery, the cancer has approximately 30% of recurrence rate after 1 year of surgery. After total removal of the cancer, the cancer cannot be visibly observed through examinations, such as computed tomographic (CT) examinations and ultrasonographic examinations. Thus, a postoperative patient should receive various anti-cancer drugs and undergo various examinations to prevent recurrence of the cancer. The patient with the possibility of recurrence remaining unknown should carry great physical, mental, and financial burdens. If the recurrence of the cancer could be accurately predicted, the burdens on the patient could be reduced.

Unfortunately, none of the scoring systems meet the needs of clinical practice. One of reasons is that the discriminant features used in the scoring systems are not deciding factors in the prediction of recurrence, because the discriminant features used in the scoring systems have been determined through trial and error by medical doctors. Thus, the optimality of the discriminant features is not theoretically assured. In addition, the discriminant features used in the scoring systems are preliminarily determined for each scoring system. Thus, if any of the data on the discriminant features used in a scoring system is defective, the corresponding scoring systems cannot be used.

The predictability of the scoring system may be improved through the use of molecular discriminant features, such as genetic mutations associated with cancer that is discovered through cutting-edge molecular life sciences. Unfortunately, many of such molecular discriminant features are not covered by so-called "health insurance". Being covered by health insurance requires an approval of the drug legislation through clinical trials. Thus, enormous research funding and a long time are required until molecular discriminant features can be applied to patients.

As described above, there is a strong need in clinical practice for selection of discriminant features required for prediction of recurrence of a disease in a patient who received surgery (treatment) for the disease or reliable predication of recurrence of the disease based on previous clinical data of the patient.

CITATION LIST

Patent Literature

[PTL 1] Japanese Translation of PCT International Application Laid-Open No. 2013-532295
[NPL 1] Tateishi R, Yoshida H, Shiina S, et al: Proposal of a New Prognostic Model for Hepatocellular Carcinoma-an Analysis of 403 Patients. Gut 54: 419-425, 2005.
[NPL 2] Ikai H, Takayasu K, Omata M, et al: A modified Japan Integrated Stage Score for Prognostic Assessment in Patients with Hepatocellular Carcinoma. J Gastroenterology 41, 884-892, 2006.
[NPL 3] M. Minagawa, I. Ikai, Y. Matsuyama, Y. Yamaoka, M. Makuuchi, Staging of Hepatocellular Carcinoma Assessment of the Japanese TNM and AJCC/UICC TNM Systems in a Cohort of 13,772 Patients in Japan, Annals of Surgery, Vol. 245, No. 6, pp. 909-922, June 2007.
[NPL 4] J M Henderson, M. Sherman, A. Tavill, M. Abecassis, G. Chejfec, and T. Gramlich, AHPBA/AJCC Consensus Conference on Staging of Hepatocellular Carcinoma: Consensus Statement, HPB, Vol. 5, No. 4, pp. 243-250, 2003.

SUMMARY OF INVENTION

Technical Problem

The purpose of the present invention is to solve the problem described above and to provide an information processor, a program for processing information, and a method of processing information that support reliable prediction of the occurrence of a specific event based on past statistical information including qualitative data as well as quantitative data.

Solution to Problem

An information processor according to the present invention determining whether an input pattern corresponding to an input object to be recognized belongs to a specific class among multiple classes based on feature subsets of any combination of a plurality of features, each feature comprises multiple categories, the information processor including a storage storing the input pattern corresponding to the input object and samples corresponding to respective sample objects; and a classification determiner determining whether the input pattern belongs to the specific class based on the categories of the respective features corresponding to the input pattern. The input pattern is associated with feature information indicating the categories of the respective features into which the data of the input pattern are classified. Each of samples is associated with feature information also indicating the categories of the respective features into which the data of the samples are classified and class label information indicating whether the samples belong to the specific class. The classification determiner calculates a first conditional probability and a second conditional probability based on the number of the samples belonging to each category of the respective features, the first conditional probability is a probability that the data of the input pattern belong to categories corresponding to the respective features for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples, and determines whether the input pattern belongs to the specific class based on the feature information on the input pattern, the first conditional probability and the second conditional probability.

Advantageous Effects of Invention

According to the present invention, reliable prediction of the occurrence of a specific event can be theoretically supported based on past statistical information including qualitative data.

BRIEF DESCRIPTION OF DRAWINGS

FIG. 2 is a schematic diagram illustrating an example of samples stored in the information processor illustrated in FIG. 1.

FIG. 3 is a schematic diagram illustrating an example of class label information on the samples stored in the information processor illustrated in FIG. 1.

FIG. 4 is a schematic diagram illustrating an example of feature information on the samples stored in the information processor illustrated in FIG. 1.

FIG. 5 is a schematic diagram illustrating an example of the number of training samples belonging to the categories of the respective features of training samples extracted from the samples stored in the information processor illustrated in FIG. 1.

FIG. 8 is a schematic diagram illustrating the relation between the categories corresponding to the respective features of test samples extracted from the samples stored in the information processor illustrated in FIG. 1, class label information, classification information, and judgement information.

FIG. 11 is a schematic diagram illustrating another example of screen displaying discriminant features determined by the information processor illustrated in FIG. 1.

FIG. 12 is a schematic diagram illustrating another example of screen displaying discriminant features determined by the information processor illustrated in FIG. 1.

DESCRIPTION OF THE PREFERRED EMBODIMENT

Embodiment of an information processor, a program for processing information, and a method of processing information according to the present invention will now be described with reference to the attached drawings.

The present invention supports accurately predicting whether a specific event occurs among multiple events, using numerical values determined by data indicating past results, based on the discrete Bayes decision rule in statistical pattern recognition having a clear mathematical base.

The following embodiments of the present invention will now be described with an example of the case predicting whether liver cancer will recur in a patient who has received surgery using the clinical data of a liver cancer patient who is the target of the prediction (hereinafter referred to as "test patient") and the clinical data and the post-surgery progress of another patient (hereinafter referred to as "sample patient") who has received surgery to remove liver cancer (hereinafter referred to as "surgery").

The present invention can be applied to an input object that is to be recognized whether the input object belongs to a specific class or not. It should be noted that the embodiments of the present invention should not be construed to limit the applicable scope of the invention.

The information processor according to the present invention further represents the uncertainty of the recurrence of the liver cancer in the test patient in the numeric form of the posterior probability calculated using samples (sample-data) corresponding to the sample patients and input pattern (input-data) corresponding to the test patient, as described below. The information processor according to the present invention enhances the reliability of the prediction through the discrete Bayes decision rule using the posterior probability in statistical pattern recognition.

The information processor according to the present invention also represents the uncertainty of the selection of effective examination items used in the prediction of the recurrence of liver cancer among multiple examination items in the numeric form of the posterior probability calculated using the samples, as described below. The examination items are examples of features in the present invention. The information processor according to the present invention enhances the reliability of the selection of discriminant features through the discrete Bayes decision rule using the posterior probability in statistical pattern recognition.

Information Processor

Figure 1:
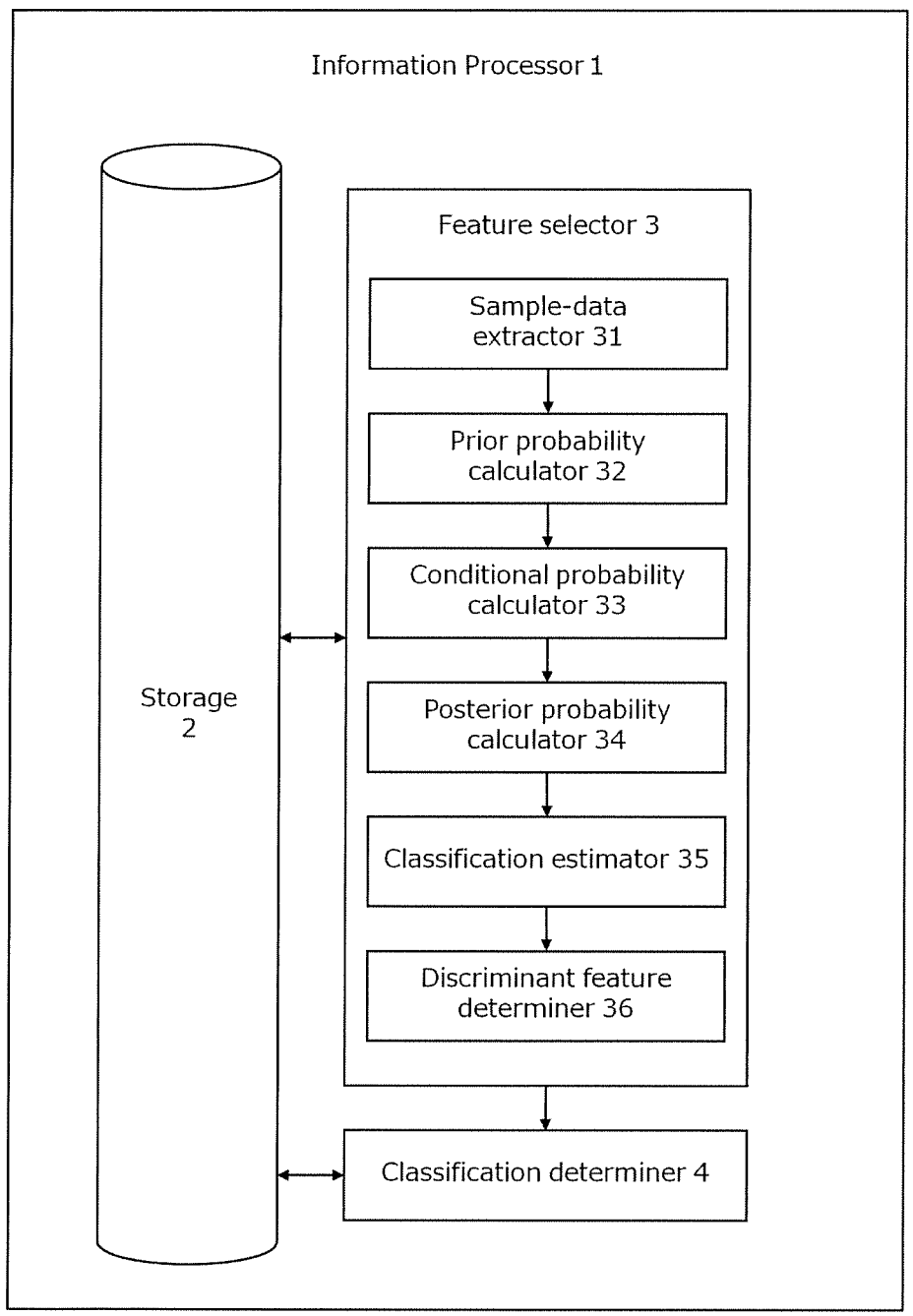
FIG. 1 is a block diagram illustrating an embodiment of an information processor according to the present invention.

FIG. 1 is a block diagram indicating an information processor (hereinafter referred to as "processor") according to an embodiment of the present invention. The processor 1 includes a storage 2, a feature selector 3, and a classification determiner 4. The feature selector 3 includes a sample-data extractor 31, a prior probability calculator 32, a conditional probability calculator 33, a posterior probability calculator 34, a classification estimator 35, and a discriminant feature determiner 36.

The processor 1 is a personal computer, for example. In the processor 1, a program for processing information (hereinafter referred to as "program") according to the present invention operates in cooperation with the hardware resource of the processor 1 to carry out a method of processing information (hereinafter referred to as "method") according to the present invention described below.

Alternatively, the program may be executed by causing a computer (not shown) to function in the same way with the processor 1 and can perform the method.

The storage 2 stores information used by the processor 1 to execute the method described below, such as samples and the input pattern.

The sample-data contains examination information and class label information on a sample patient.

The examination information represents the clinical data for respective examination items. The examination items include qualitative examination items and quantitative examination items. Clinical data for qualitative examination items are represented by non-numeric values, such as gender, lymphatic invasion, ulcer, venous invasion, the invasion depth of tumor and the degree of tumor differentiation. Clinical data for quantitative examination items are represented by numerical values, such as the number of tumor sites, the size of the tumor, bilirubin level, and albumin level. In the present invention, all examination information represented by the categories of respective examination items described below are discrete. That is, the discrete Bayes decision rule in the present invention can be applied to qualitative data, unlike the ordinary Bayes decision rule.

The class label information indicates whether a specific event has occurred for a sample of interest.

A specific event refers to "recurrence of liver cancer within one year after surgery." That is, the class label information indicates "whether liver cancer recurred within one year after surgery."

The input-data contains examination information on the test patient.

FIG. 2 is a schematic diagram indicating the example of the samples stored in the storage 2.

The storage 2 stores available samples. Each sample is stored in correlation with a sample identifier (sample ID). That is, the processor 1 can retrieve a sample corresponding to a sample ID from the storage 2 using the sample ID. The examination information contained in the sample is stored in the storage 2 in correlation with a feature identifier (feature ID) specifying an examination item. FIG. 2 indicates that the clinical data for an examination item corresponding to the feature ID "$X_1$" is "$V_{11}$" and the clinical data for an examination item corresponding to the feature ID "$X_2$" is "$V_{21}$," in a sample-data corresponding to the sample ID "$D_1$," for example.

FIG. 3 is a schematic diagram indicating the example of class label information.

The class label information "$\omega_1$" is "the information indicating that liver cancer has recurred within one year after surgery." The class label information "$\omega_2$" is "the information indicating that liver cancer has not recurred within one year after surgery." FIG. 3 indicates that the class label information on the sample patient corresponding to the sample ID "$D_1$" is "$\omega_2$," that is, the patient had not experienced recurrence of liver cancer within one year after surgery, for example. Each sample patient is assigned to the class "liver cancer has recurred within one year after surgery" (hereinafter referred to as "specific class") or the class "liver cancer has not recurred within one year after surgery" (hereinafter referred to as "non-specific class").

The feature selector 3 selects the features as the discriminant features that are suitable for the prediction of liver cancer from among multiple examination items. The method of selecting the features as discriminant features will be described below.

The classification determiner 4 predicts recurrence of liver cancer in a test patient. A method of predicting accurately the recurrence of liver cancer will be described below.

The sample-data extractor 31 extracts part of the samples as training samples and the remaining samples as test samples.

The prior probability calculator 32 calculates the probability of the specific class occurring (hereinafter referred to "first prior probability") and the probability of the non-specific class occurring (hereinafter referred to "second prior probability").

The conditional probability calculator 33 calculates the first conditional probability and the second conditional probability.

The first conditional probability of a test patient is a probability that the data of the test patient belong to categories corresponding to the respective discriminant features for the specific class (the first conditional probability is the probability in the case that the specific class is occurred). The first conditional probability is calculated using the feature information and the feature subset. The first conditional probability is calculated for categories in the feature information on features included in the feature subset. The feature information and the feature subset will be described below.

The second conditional probability is a probability that the data of the test patient belong to categories corresponding to the respective discriminant features for the non-specific class (the second conditional probability is the probability in the case that the non-specific class is occurred). The second conditional probability is calculated using the feature information and the feature subset. The second conditional probability is calculated for categories in the feature information on features included in the feature subset.

The feature information is the information, provided for each sample (training sample or test sample), indicating the "categories of each feature or examination item" to which the examination information contained in the sample-data is belonged.

Any examination item is divided into mutually exclusive categories. The categories of each examination item are information specifying each category. That is, the clinical data of a patient belongs to any one of categories for each examination item. For example, the examination item corresponding to "gender" is divided into two categories, "male" and "female." The examination item corresponding to "the number of tumor sites" is divided into three categories, "less than two," "two or more than two but less than seven," and "seven or more", for example.

The feature subset consists of one examination item or a combination of two or more examination items selected from multiple examination items.

FIG. 4 is a schematic diagram indicating the example of feature information on the training samples stored in the storage 2.

FIG. 4 indicates that the examination item corresponding to the feature ID "$X_1$" is divided into two categories and the category identifiers (category IDs) specifying each category are "$X_{1(1)}$" and "$X_{1(2)}$". FIG. 4 indicates that the examination item corresponding to the feature ID "$X_2$" is divided into three categories and the category IDs specifying each category are "$X_{2(1)}$," "$X_{2(2)}$," and "$X_{2(3)}$". FIG. 4 indicates that the training sample of the sample ID "$D_{t1}$" belongs to the category corresponding to the category ID "$X_{1(2)}$" for the examination item corresponding to the feature ID "$X_1$" and belongs to the category corresponding to the category ID "$X_{2(2)}$" for the examination item corresponding to the feature ID "$X_2$."

The information specifying the categories of each examination item are preliminarily stored in the storage 2, for example, information specifying the two categories "male" and "female" for the examination item of "gender" and information specifying the three categories "less than three," "three or more than three but less than seven," and "seven or more" for the examination item of "the number of tumor sites."

The processor 1 generates the feature information on the training samples from the clinical data of respective training samples with reference to the information specifying the categories of each examination item stored in the storage 2 and stores the generated feature information in the storage 2.

FIG. 5 is a schematic diagram indicating the example of the number of the training samples (the number of sample patients corresponding to the training samples (hereinafter referred to as "training patients")) belonging to respective categories of the examination items stored in the storage 2. FIG. 5 indicates that the number of training samples belonging to the categories of the respective features is stored in the storage 2 for each class.

FIG. 5 indicates that the number of training samples (training patients) belonging to the category corresponding to the category ID "$X_{1(1)}$" of the examination item corresponding to the feature ID "$X_1$" is "$n^1_{1(1)}$" and the number of training samples belonging to the category corresponding to the category ID "$X_{1(2)}$" is "$n^1_{1(2)}$," among the training samples belonging to the class corresponding to the class ID "$\omega_1$." FIG. 5 indicates that the number of training samples belonging to the category corresponding to the category ID "$X_{2(1)}$" of the examination item corresponding to the feature ID "$X_2$" is "$n^1_{2(1)}$," the number of training samples belonging to the category corresponding to the category ID "$X_{2(2)}$" is "$n^1_{2(2)}$," and the number of training samples belonging to the category corresponding to the category ID "$X_{2(3)}$" is "$n^1_{2(3)}$," among the training samples belonging to the class corresponding to the class ID "$\omega_1$."

The number of training samples in each examination item belonging to the class corresponding to the class ID "$\omega_1$" is constant in any examination item. That is, the following equation holds.

$$n^1_{1(1)} + n^1_{1(2)} = n^1_{2(1)} + n^1_{2(2)} + n^1_{2(3)}$$

The processor 1 counts the number of training samples belonging to each category of each examination item for each class using the feature information and the class label information on the training samples and stores the counted number of training samples in the storage 2.

The processor 1 calculates the conditional probabilities (first and second conditional probabilities) using the number of training samples belonging to each category corresponding to each discriminant feature.

The $r_{tj}$th category of the examination item $x_{tj}$ is represented by $x_{tj(rtj)}$. The subscript tj is the identification number (feature ID) of the examination item, which is $t_j \in \{1, 2, \ldots, M\}$. Assuming that d discriminant features are selected, the patient is represented by a d-dimensional vector $X = [x_{t1(rt1)}, x_{t2(rt2)}, \ldots x_{td(rtd)}]^T$. $A^T$ represents the transposition of a matrix A. The conditional probability $P(x_{tj(rtj)}|\omega_i)$ for the category $x_{tj(rtj)}$ is defined by Expression 1.

$$P\left(x_{t_j(r_{t_j})} \mid \omega_i\right) = \frac{n^i_{t_j(r_{t_j})}}{\sum_{k=1}^{d} n^i_{t_k(r_{t_k})}} \quad j = 1, 2, \ldots, d \quad \text{(Expression 1)}$$

$n^i_{tj(rtj)}$ represents the number of training samples belonging to the category $x_{tj(rtj)}$ among $n^i$ training samples of the class $\omega_i$.

In general, Expression 2 holds, assuming the case where events that the clinical data for an examination item belonging to any of multiple categories are independent from each other.

$$\begin{aligned} P(x \mid \omega_i) &= P\left(x_{t_1(r_{t_1})}, x_{t_2(r_{t_2})}, \ldots x_{t_d(r_{t_d})_{t_2(r_{t_2})}} \mid \omega_i\right) \\ &= P\left(x_{t_1(r_{t_1})} \mid \omega_i\right) P\left(x_{t_2(r_{t_2})} \mid \omega_i\right) \ldots P\left(x_{t_d(r_{t_d})} \mid \omega_i\right) \\ &= \prod_{k=1}^{d} P\left(x_{t_k(r_{t_k})} \mid \omega_i\right) \end{aligned} \quad \text{(Expression 2)}$$

In a two-class problem in which an event belongs to any of two classes $\omega_1$ and $\omega_2$, the posterior probability $P(\omega_i|X)$ is defined as Expression 3 by the Bayes theorem.

$$P(\omega_i \mid x) = \frac{P(\omega_i) P(x \mid \omega_i)}{P(\omega_1) P(x \mid \omega_1) + P(\omega_2) P(x \mid \omega_2)} \quad \text{(Expression 3)}$$

Assuming that a prior probability $P(\omega_i)$ is an equal probability of 0.5, the posterior probability $P(\omega_i|X)$ in Expression 3 is defined by Expression 4.

$$P(\omega_i \mid x) = \frac{P(x \mid \omega_i)}{P(x \mid \omega_1) + P(x \mid \omega_2)} \quad \text{(Expression 4)}$$

The posterior probability $P(\omega_i|X)$ is defined by Expression 5 by substituting Expression 2 into Expression 4.

$$P(\omega_i \mid x) = \frac{\prod_{k=1}^{d} P\left(x_{t_k(r_{t_k})} \mid \omega_i\right)}{\prod_{k=1}^{d} P\left(x_{t_k(r_{t_k})} \mid \omega_1\right) + \prod_{s=1}^{d} P\left(x_{t_s(r_{t_s})} \mid \omega_2\right)} \quad \text{(Expression 5)}$$

In the case where the examination items are $X_1$ and $X_2$, in other words, d=2, the clinical data of the training sample belong to $X_{1(1)}$ and $X_{2(3)}$. At this time, Expression 6 holds.

$$P(x_{1(1)} \mid \omega_1) = \frac{n^1_{1(1)}}{n^1_{1(1)} + n^1_{2(3)}}$$ (Expression 6)

$$P(x_{2(3)} \mid \omega_1) = \frac{n^1_{2(3)}}{n^1_{1(1)} + n^1_{2(3)}}$$

Thus, the conditional probability $P(X_{1(1)}, X_{2(3)} \mid \omega_i)$ in Expression 5 is calculated by Expression 7.

$$P(x_{1(1)}, x_{2(3)} \mid \omega_1) = P(x_{1(1)} \mid \omega_1) P(x_{2(3)} \mid \omega_1)$$ (Expression 7)

Similarly, the processor 1 calculates the conditional probability $P(X_{1(1)}, X_{2(3)} \mid \omega_2)$ and then calculates the posterior probabilities for the classes $\omega_1$ and $\omega_2$ by expression 5. The processor 1 compares the calculated posterior probabilities for the respective classes and assigns the input pattern (test patient) to the class having the larger posterior probability.

Method of Processing Information

The method carried out by the processor 1 according to an embodiment will now be described.

Figure 6:
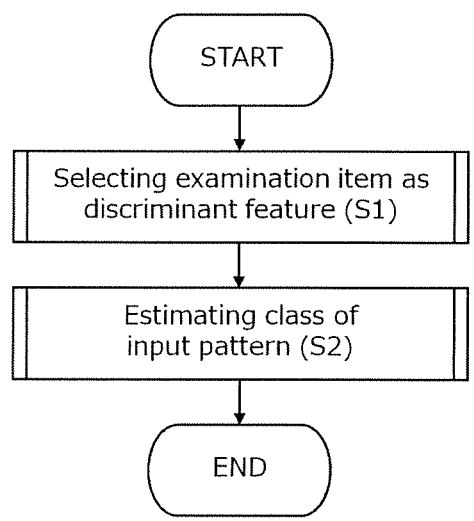
FIG. 6 is a flow chart illustrating an example of method of processing information according to the present invention.

FIG. 6 is a flow chart indicating the method according to an embodiment.

The processor 1 first, using the feature selector 3, selects effective examination items, which are called discriminant features, suitable for the prediction of recurrence of liver cancer from multiple examination items (S1).

The processor 1 then, using the classification determiner 4, determines the class of the input pattern (test patient) using the discriminant features, in other words, predicts whether the test patient corresponding to the input pattern will experience recurrence of liver cancer within one year after surgery (S2).

Selection of Feature

Figure 7:
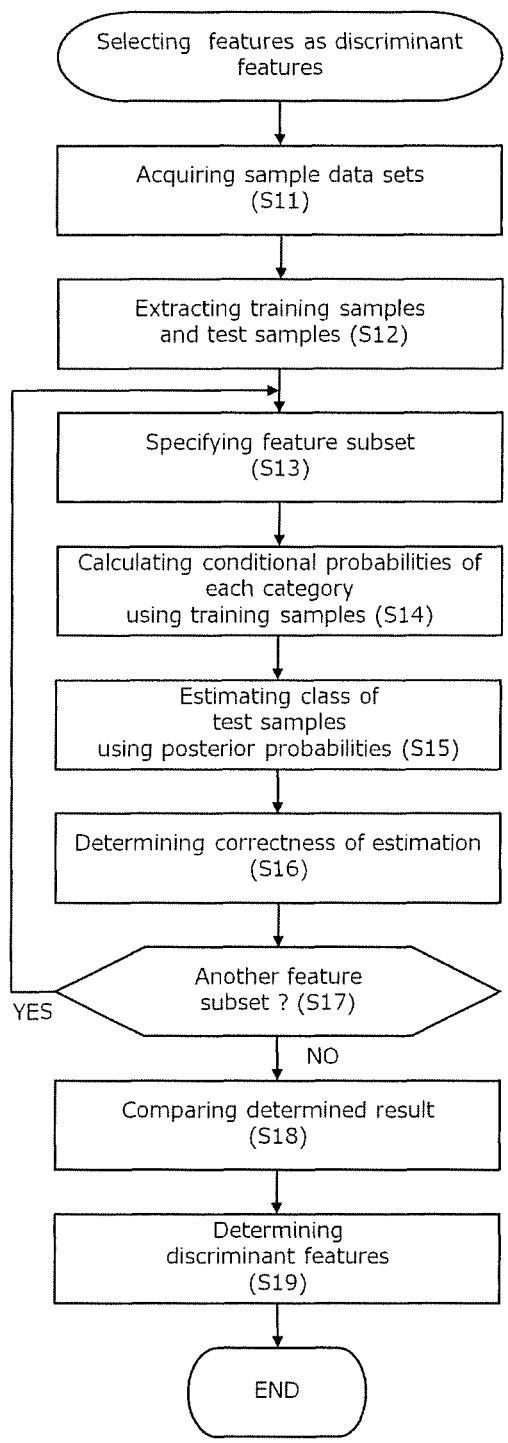
FIG. 7 is a flow chart illustrating an example of process of selecting features as discriminant features in the method of processing information illustrated in FIG. 6.

FIG. 7 is a flow chart indicating the example of process (S1) of selecting effective examination items that the processor 1 instructs using the feature selector 3, as discriminant features.

The processor 1 first acquires the sample-data (samples) stored in the storage 2 (S11) using the sample-data extractor 31, extracts part of the samples from all of the available samples as training samples, and extracts the remaining samples as test samples (S12). The processor 1 extracts 80 samples from the 100 acquired samples as training samples and extracts the remaining 20 samples as test samples, for example. The processor 1 randomly extracts training samples and test samples from the samples without referring to the content (clinical data) of the samples. The number of training samples and the number of test samples extracted by the processor 1 and/or the ratio of the number of training samples to the number of test samples are preliminarily stored in the storage 2. The processor 1 extracts the samples based on the numbers and/or the ratio stored in the storage 2.

It should be noted that, according to the present invention, the number of test samples extracted from the samples may not be all of the samples remaining after extraction of the training samples from the available samples. That is, the processor may extract 80 samples as training samples from the 100 samples and extract 15 samples as test samples from the remaining 20 samples, for example.

The processor 1 then specifies feature subsets of any of examination items (S13). In the case where the examination items are $X_1$, $X_2$, and $X_3$, the feature subsets specified by the processor 1 are $(X_1)$, $(X_2)$, $(X_3)$, $(X_1, X_2)$, $(X_1, X_3)$, $(X_2, X_3)$, and $(X_1, X_2, X_3)$, for example.

It should be noted that the number of discriminant features specified by the processor 1 may be preliminarily determined and stored in the storage 2 so that the number of the discriminant features is possible to refer when the processor 1 specifies the feature subsets. That is, in the case where the number of discriminant features is "two" and three features $X_1$, $X_2$, and $X_3$ are used, the processor 1 specifies $(X_1, X_2)$ and $(X_1, X_3)$ as two feature subsets, for example.

The processor 1 then, using the conditional probability calculator 33, calculates the conditional probabilities (the first and second conditional probabilities) of each category of the features contained in feature subsets from expression 1 based on the training samples (S14).

The processor 1 then, using the posterior probability calculator 34, calculates the posterior probability of each class for respective test samples, from Expression 5.

It should be noted that, in this embodiment, the prior probabilities for a specific class and a non-specific class are the same probability (0.5). Thus, the processor 1 calculates the posterior probability from Expression 5 without calculating prior probabilities (first and second prior probabilities).

The processor 1 then, using the classification estimator 35, estimates the class of the test samples based on the posterior probabilities calculated for the respective classes (S15), and determines the correctness of the estimation (S16).

The processor 1 compares the posterior probabilities calculated for the respective classes, and estimates the class having a larger posterior probability as the class of the test sample, for example.

The processor 1 compares the classification information indicating the estimated class with the class label information on the test sample stored in the storage 2 as sample-data, and determines the correctness of the estimated class of the test sample based on whether both information match. That is, if both information match, the estimated class of the test sample is determined to be correct, whereas if both information do not match, the estimated class of the test sample is determined to be incorrect.

FIG. 8 is a schematic diagram indicating the examination items contained in the specified feature subsets are "$X_1$, $X_2$, . . .", and indicating the relation between the categories of the respective examination items to which the test samples corresponding to the sample IDs "$D_{e1}$, $D_{e2}$, . . . " belong, the class label information on the respective test samples, the classification information indicating the class of the respective test samples estimated by the processor 1, and the judgement information indicating the correctness of the estimation determined by the processor 1.

FIG. 8 indicates that the test sample corresponding to the sample ID "$D_{e1}$" has class label information classified into a class ID "$\omega_1$," classification information classified into a class ID "$\omega_1$," and judgement information "T" indicating correctness. That is, the processor 1 correctly estimates that the patient corresponding to the test sample of the sample ID "$D_{e1}$" had experienced the recurrence of liver cancer within one year after surgery.

FIG. 8 indicates that the test sample corresponding to the sample ID "$D_{e2}$" has class label information classified into a class ID "$\omega_2$," classification information classified into a class ID "$\omega_1$," and judgement information "F" indicating incorrectness. That is, the processor 1 does not correctly estimate that the patient corresponding to the test sample of the sample ID "$D_{e2}$" had not experienced the recurrence of liver cancer within one year after surgery.

The processor 1 carries out steps S14 to S16 for all of the feature subsets (S17).

The processor 1 then, using the discriminant feature determiner 36, compares the determined results on the correctness of the estimations for the respective feature subsets (S18) and determines discriminant features (S19).

The processor 1 adds the judgement information on the test samples by the feature subset, and determines the effective examination items contained in the feature subset having the maximum number of test samples determined to be correct estimation, as discriminant features, for example.

Class Determination of Input Pattern

Figure 9:
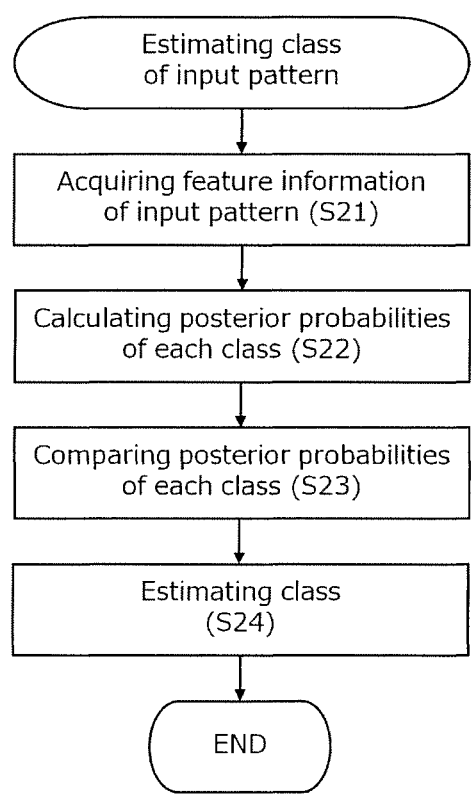
FIG. 9 is a flow chart illustrating an example of process of estimating the class of the input pattern in the method of processing information illustrated in FIG. 6.

FIG. 9 is a flow chart indicating an example of process of determining the class (S2) of input pattern that the processor 1 carries out using the classification determiner 4.

The processor 1 first acquires the feature information on the input pattern (S21). The feature information on the input pattern is the information indicating "the category of each examination item" into which the data of the input pattern are classified, similar to the feature information on the samples described above. The processor 1 reads the input pattern and the information specifying the categories of the respective examination items corresponding to the discriminant features, from the storage 2. The processor 1 specifies the category into which the data of the input pattern are classified by the effective examination items selected as the discriminant features and acquires the feature information on the input pattern.

The processor 1 then calculates the posterior probabilities for the respective classes of the input pattern from Expression 5 using the conditional probabilities (calculated through the same process as that in step S14) for the respective categories of the discriminant features determined using the training samples (S22).

The processor 1 then compares the calculated posterior probabilities for the respective classes (S23).

The processor 1 then specifies the class of the input pattern, that is, estimates the class of the input pattern as a specific class or a non-specific class (S24).

The processor 1 compares the posterior probabilities for the respective classes and estimates the class corresponding to the posterior probability having the maximum value as the class of the input pattern, for example.

The specified class of the input pattern is stored in the storage 2 in correspondence with the input pattern. The specified class of the input pattern is output to a display (not shown) of the processor 1, so that a message, for example, "patient AAA has low probability of recurrence of liver cancer within one year after surgery," appears on the display.

Figure 10:
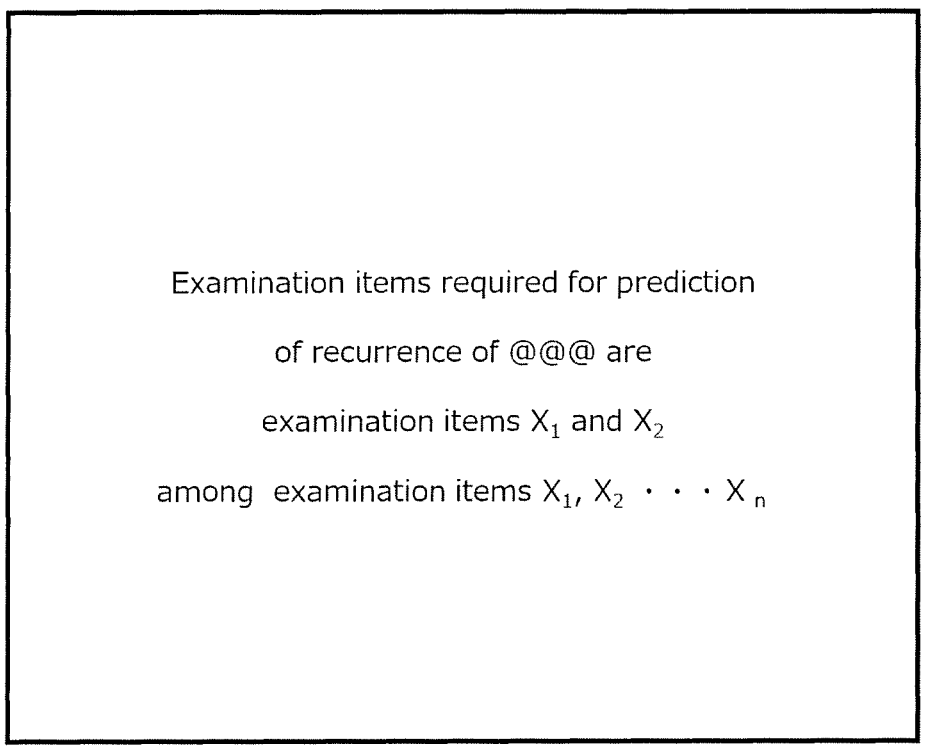
FIG. 10 is a schematic diagram illustrating an example of a screen displaying discriminant features determined by the information processor illustrated in FIG. 1.

FIG. 10 is a schematic diagram indicating the example of screen displaying the discriminant features determined by the processor 1. FIG. 10 indicates that the effective examination items $X_1$ and $X_2$ are selected from the examination items $X_1, X_2, \ldots, X_n$ as discriminant features.

FIG. 11 is a schematic diagram indicating another example of screen displaying the discriminant features determined by the processor 1. FIG. 11 indicates that the feature subsets of the effective examination items selected from the examination items $Y_1, Y_2, Y_3, \ldots, Y_n$ and the posterior probabilities of the respective feature subsets are displayed in a descending order of the posterior probabilities. The processor 1 can let the user of the processor 1 check the difference in the subsets through the difference in the values of the posterior probabilities by prompting the user to view the screen, for example.

FIG. 12 is a schematic diagram indicating another example of screen displaying the discriminant features determined by the processor 1. FIG. 12 indicates that the accuracy of prediction of recurrence of a particular disease in a patient who had received examinations corresponding to the examination items $Z_1$ and $Z_2$ can improve by additional examination corresponding to examination item $Z_3$. The processor 1 can specify the correspondence between the feature subsets of the examination items and the posterior probabilities as indicated in FIG. 11, and the feature subset of the examination items having posterior probabilities higher than those of the feature subsets of the examination items of examinations that have been conducted on a patient. Then, the processor 1 can extract the examination items other than the examination items of examinations that have been conducted on the patient from the combinations included in the specified examination items, for example.

CONCLUSION

According to the embodiments described above, the effectiveness of examination items used in the prediction of recurrence of liver cancer can be compared using the posterior probabilities. As a result, the present invention can support the reliable prediction of recurrence of liver cancer based on the numerical values.

It should be noted that the embodiments described above deal with two classes, "specific class" and "non-specific class." Alternatively, the present invention may deal with three or more classes.

In the case where multiple events corresponding to the respective classes $\omega_1, \omega_2, \ldots, \omega_m$ (m≥3) are mutually exclusive events and the input pattern belongs to one of the m classes. At this time, in the case where the effective examination items or discriminant features $X_{t1(rt1)}, X_{t2(rt2)}, \ldots, X_{td(rtd)}$ are used, the processor calculates the conditional probabilities $P(X_{t1(rt1)}, X_{t2(rt2)}, \ldots, X_{td(rtd)} | \omega_i)$ (i=1, 2, ..., m) for the respective classes and then calculates the posterior probabilities $P(\omega_i | X_{t1(rt1)}, X_{t2(rt2)}, \ldots, X_{td(rtd)})$ from Expression 8.

$$P(\omega_i \mid x_{t_1(r_{t_1})}, x_{t_2(r_{t_2})}, \ldots x_{t_d(r_{t_d})}) = \frac{\prod_{j=1}^{d} P(x_{t_j(r_{t_j})} \mid \omega_i)}{\prod_{k=1}^{m} \prod_{j=1}^{d} P(x_{t_j(r_{t_j})} \mid \omega_k)} \quad \text{(Expression 8)}$$

In the case where Expression 9 holds for the posterior probabilities $P(\omega_i | X_{t1(rt1)}, X_{t2(rt2)}, \ldots, X_{td(rtd)})$ of the input pattern $X=[X_{t1(rt1)}, X_{t2(rt2)}, \ldots, X_{td(rtd)}]$, the processor determines the class $\omega_k$ as the class of the input pattern X.

$$\max_i P(\omega_i \mid x_{t_1(r_{t_1})}, x_{t_2(r_{t_2})}, \ldots x_{t_d(r_{t_d})}) = \quad \text{(Expression 9)}$$
$$P(\omega_k \mid x_{t_1(r_{t_1})}, x_{t_2(r_{t_2})}, \ldots x_{t_d(r_{t_d})})$$

The aspects of the processor, the program, and the method described above will be summarized below.

(Aspect 1)

An information processor determining whether an input pattern corresponding to an input object belongs to a specific class among multiple classes, based on feature subsets of any combination of a plurality of features, each feature comprises multiple categories, the information processor comprising:

a storage storing the input pattern corresponding to the input object and samples corresponding to respective sample objects; and a classification determiner determining whether the input pattern belongs to the specific class based on the categories of the respective features into which data of the input pattern are classified, wherein the input pattern is associated with feature information indicating the categories of the respective features into which the data of the input pattern are classified, each of samples is associated with feature information indicating the categories of the respective features into which the data of the samples are classified and class label information indicating whether the samples belong to the specific class, and the classification determiner calculates a first conditional probability and a second conditional probability based on the number of the samples belonging to each category of the respective features, the first conditional probability is a probability that the data of the input pattern belong to categories corresponding to the respective features for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples, and determines whether the input pattern belongs to the specific class based on the feature information on the input pattern, the first conditional probability and the second conditional probability.

(Aspect 2)

The information processor according to Aspect 1, wherein the classification determiner calculates a first posterior probability that the input pattern belongs to the specific class based on the feature information on the input pattern, a first prior probability of occurrence of the specific class and the first conditional probability, calculates a second posterior probability that the input pattern belongs to the non-specific class based on the feature information on the input pattern, a second prior probability of occurrence of the non-specific class and the second conditional probability, and determines whether the input pattern belongs to the specific class by comparing the first posterior probability with the second posterior probability.

(Aspect 3)

The information processor according to Aspect 1, wherein qualitative features are comprised in the features.

(Aspect 4)

The information processor according to Aspect 3, wherein quantitative features are comprised in the features.

(Aspect 5)

The information processor according to Aspect 1, further comprising:

a feature selector selecting a discriminant feature subset from the feature subsets, wherein the classification determiner determines whether the input pattern belongs to the specific class based on the categories of the respective discriminant features included in the discriminant feature subset into which the data of the input pattern are classified.

(Aspect 6)

The information processor according to Aspect 5, wherein the feature selector selects the discriminant feature subset based on the first conditional probability and the second conditional probability.

(Aspect 7)

The information processor according to Aspect 6, wherein, the feature selector comprises:

(a) a sample-data extractor extracting part of the samples as training samples and the remaining samples as test samples, from samples;

(b) a classification estimator estimating whether the test samples corresponding to the test objects belong to the specific class, based on the feature information on the training samples, the class label information on the training samples, and the feature information on the test samples, for respective feature subsets of any of the features, and determining the correctness of the estimation based on the class label information on the test samples; and (c) a discriminant feature determiner determining the discriminant feature subset based on the determined result of the correctness of the estimation for each feature subset, and the classification estimator estimates whether the test samples corresponding to the test objects belong to the specific class based on the first conditional probability and the second conditional probability.

(Aspect 8)

The information processor according to Aspect 7, wherein the sample-data extractor extracts the test samples from the samples, the classification estimator outputs judgement information indicating the correctness of the estimation of the respective test samples based on the first conditional probability and the second conditional probability, and the discriminant feature determiner determines the discriminant feature subset based on the judgement information of the respective test samples.

(Aspect 9)

A program for processing information instructing a computer to function as the information processor according to Aspect 1.

(Aspect 10)

A method of processing information carried out by an information processor determining whether an input object belongs to a specific class among multiple classes, based on feature subsets of any combination of a plurality of features, each feature comprises multiple categories, the information processor comprising:

a storage storing input pattern corresponding to the input object and samples corresponding to respective sample objects; and a classification determiner determining whether the input pattern belongs to the specific class based on the categories of the respective features into which data of the input pattern are classified, the input pattern is associated with feature information indicating the categories of the respective features into which the data of the input pattern are classified, each of samples is associated with feature information indicating the categories of the respective features into which the data of the samples are classified and class label information indicating whether the samples belong to the specific class, the method carried out by the information processor comprising:

a step of calculating a first conditional probability and a second conditional probability based on the number of the samples belonging to each category of the respective features, the first conditional probability is a probability that the data of the input pattern belong to categories corresponding to the respective features for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples; and a step of determining whether the input pattern belongs to the specific class based on the feature information on the input pattern, the first conditional probability and the second conditional probability.

(Aspect 11)

An information processor determining whether an input pattern corresponding to an input object belongs to a specific class among multiple classes, based on discriminant features selected from multiple features with multiple categories, the information processor comprising:

a feature selector selecting the discriminant features from features;

a classification determiner determining whether the input pattern corresponding to the input object belongs to the specific class, based on the categories of the respective features included in the discriminant features into which the data of the input pattern are classified; and a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant features, the feature selector comprising:
(a) a sample-data extractor extracting part of the samples as training samples and the remaining samples as test samples, from the samples;
(b) a classification estimator estimating whether the test samples corresponding to test objects belong to the specific class based on the feature information on the training samples, the class label information on the training samples, and the feature information on the test samples, for respective feature subsets of any combination of the features, and determining the correctness of the estimation based on the class label information on the test samples; and
(c) a discriminant feature determiner determining the discriminant features based on the correctness of the estimation for each of feature subsets, wherein, the classification estimator (b-1) calculates a first conditional probability and a second conditional probability based on the number of the training samples belonging to each category of the respective features, the first conditional probability is a probability that data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples, (b-2) calculates a first posterior probability that the test sample corresponding to the test object belongs to the specific class based on the feature information on the test sample, a first prior probability of occurrence of the specific class and the first conditional probability, (b-3) calculates a second posterior probability that the test sample corresponding to the test object belongs to the non-specific class based on the feature information on the test sample, a second prior probability of occurrence of the non-specific class and the second conditional probability, (b-4) outputs classification information indicating a result of an estimation on whether the test samples corresponding to the test objects belong to the specific class by comparing the first posterior probability with the second posterior probability, and (b-5) outputs judgement information indicating the correctness of the estimation by comparing the classification information of the test samples with the class label information on the test samples, and the discriminant feature determiner (c-1) specifies the feature subsets corresponding to the judgement information satisfying a predetermined condition among the judgement information of the respective feature subsets, and (c-2) determines the features included in the specified feature subsets as the discriminant features.

(Aspect 12)

The information processor according to Aspect 11, wherein the classification estimator calculates the first prior probability and the second prior probability.

(Aspect 13)

The information processor according to Aspect 11 or 12, wherein, the sample-data extractor extracts the test samples from the samples, the classification estimator outputs the judgement information for each of the test samples, and the discriminant feature determiner determines the discriminant features, based on the judgement information of each of the test samples.

(Aspect 14)

The information processor according to Aspect 13, wherein, the classification estimator calculates the first conditional probability, the second conditional probability, the first posterior probability and the second posterior probability and outputs the classification information, for each of the test samples, and outputs the judgement information for each of the test samples, based on the classification information of each of the test samples.

(Aspect 15)

The information processor according to Aspect 11, wherein the first prior probability is equal to the second prior probability.

(Aspect 16)

A program for processing information instructing a computer to function as the information processor according to Aspect 11.

(Aspect 17)

A method of processing information carried out by an information processor determining whether an input pattern corresponding to an input object belongs to a specific class among multiple classes, based on discriminant features selected from multiple features with a plurality of categories, the information processor comprising:

a feature selector selecting the discriminant features from the multiple features;

a classification determiner determining whether the input pattern corresponding to the input object belongs to the specific class based on the categories of the respective features into which data of the input pattern are classified; and a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant features, the method comprising:

(a) a sample-data extraction step of extracting part of the samples as training samples and the remaining samples as test samples, from the samples;

(b) a class estimation step of estimating whether the test samples corresponding to test objects belong to the specific class based on the feature information on the training samples, the class label information on the training samples, and the feature information on the test samples, for respective feature subsets of any combination of the features, and determining correctness of the estimation based on the class label information on the test samples; and (c) a discriminant feature determination step of determining the discriminant features based on the correctness of the estimation for each of feature subsets, wherein, the class estimation step comprising:

(b-1) a step of calculating a first conditional probability and a second conditional probability based on the number of the training samples belonging to each category of the respective features, the first conditional probability is a probability that the data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples, (b-2) a step of calculating a first posterior probability that the test sample corresponding to the test object belongs to the specific class based on the feature information on the test sample, a first prior probability of occurrence of the specific class and the first conditional probability, (b-3) a step of calculating a second posterior probability that the test sample corresponding to the test object belongs to the non-specific class based on the feature information on the test sample, a second prior probability of occurrence of the non-specific class and the second conditional probability, (b-4) a step of outputting classification information indicating a result of an estimation on whether the test samples corresponding to the test objects belong to the specific class by comparing the first posterior probability with the second posterior probability, and (b-5) a step of outputting judgement information indicating the correctness of the estimation by comparing the classification information on the test samples with the class label information on the test samples, and the discriminant feature determination steps comprising:

(c-1) a step of specifying the feature subsets corresponding to the judgement information satisfying a predetermined condition among the judgement information of the respective feature subsets, and (c-2) a step of determining the features included in the specified feature subsets, as the discriminant features.

The invention claimed is:

1. An information processor determining whether an input pattern corresponding to an input object belongs to a specific class among multiple classes, based on feature subsets of any combination of a plurality of features, each feature comprises multiple categories, the information processor comprising:

a storage storing the input pattern corresponding to the input object and samples corresponding to respective sample objects; and a classification determiner determining whether the input pattern belongs to the specific class based on the categories of the respective features into which data of the input pattern are classified, wherein the input pattern is associated with feature information indicating the categories of the respective features into which the data of the input pattern are classified, each of samples is associated with feature information indicating the categories of the respective features into which the data of the samples are classified and class label information indicating whether the samples belong to the specific class, and the classification determiner calculates a first conditional probability and a second conditional probability based on the number of the samples belonging to each category of the respective features, the first conditional probability is a probability that the data of the input pattern belong to categories corresponding to the respective features for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples, and determines whether the input pattern belongs to the specific class based on the feature information on the input pattern, the first conditional probability and the second conditional probability.

2. The information processor according to claim 1, wherein the classification determiner calculates a first posterior probability that the input pattern belongs to the specific class based on the feature information on the input pattern, a first prior probability of occurrence of the specific class and the first conditional probability, calculates a second posterior probability that the input pattern belongs to the non-specific class based on the feature information on the input pattern, a second prior probability of occurrence of the non-specific class and the second conditional probability, and determines whether the input pattern belongs to the specific class by comparing the first posterior probability with the second posterior probability.

3. The information processor according to claim 1, wherein qualitative features are comprised in the features.

4. The information processor according to claim 3, wherein quantitative features are comprised in the features.

5. The information processor according to claim 1, further comprising:
a feature selector selecting a discriminant feature subset from the feature subsets,
wherein the classification determiner determines whether the input pattern belongs to the specific class based on the categories of the respective discriminant features included in the discriminant feature subset into which the data of the input pattern are classified.

6. The information processor according to claim 5, wherein the feature selector selects the discriminant feature subset based on the first conditional probability and the second conditional probability.

7. The information processor according to claim 6, wherein,
the feature selector comprises:
(a) a sample-data extractor extracting part of the samples as training samples and the remaining samples as test samples, from samples;
(b) a classification estimator estimating whether the test samples corresponding to the test objects belong to the specific class, based on the feature information on the training samples, the class label information on the training samples, and the feature information on the test samples, for respective feature subsets of any of the features, and determining the correctness of the estimation based on the class label information on the test samples; and
(c) a discriminant feature determiner determining the discriminant feature subset based on the correctness of the estimation for each feature subset, and
the classification estimator estimates whether the test samples corresponding to the test objects belong to the specific class based on the first conditional probability and the second conditional probability.

8. The information processor according to claim 7, wherein
the sample-data extractor extracts the test samples from the samples,
the classification estimator outputs judgement information indicating the correctness of the estimation of the respective test samples based on the first conditional probability and the second conditional probability, and
the discriminant feature determiner determines the discriminant feature subset based on the judgement information on the respective test samples.

9. A non-transitory computer readable medium encoded with a program for processing information instructing a computer to function as the information processor according to claim 1.

10. A method of processing information carried out by an information processor determining whether an input object belongs to a specific class among multiple classes, based on feature subsets of any combination of a plurality of features, each feature comprises multiple categories, the information processor comprising:
a storage storing input pattern corresponding to the input object and samples corresponding to respective sample objects; and
a classification determiner determining whether the input pattern belongs to the specific class based on the categories of the respective features into which data of the input pattern are classified, the input pattern is associated with feature information indicating the categories of the respective features into which the data of the input pattern are classified, each of samples is associated with feature information indicating the categories of the respective features into which the data of the samples are classified and class label information indicating whether the samples belong to the specific class, the method carried out by the information processor comprising:
a step of calculating a first conditional probability and a second conditional probability based on the number of the samples belonging to each category of the respective features, the first conditional probability is a probability that the data of the input pattern belong to categories corresponding to the respective features for the specific class, the second conditional probability is a probability that the data of the input pattern belong to categories corresponding to the respective features for a non-specific class which is a class other than the specific class among classes, and the number of the samples is counted for each class based on the feature information on the samples and the class label information on the samples; and
a step of determining whether the input pattern belongs to the specific class based on the feature information on the input pattern, the first conditional probability and the second conditional probability.

11. An information processor determining whether an input pattern corresponding to an input object belongs to a specific class among multiple classes, based on discriminant features selected from multiple features with multiple categories, the information processor comprising:
a feature selector selecting the discriminant features from features;
a classification determiner determining whether the input pattern corresponding to the input object belongs to the specific class, based on the categories of the respective features included in the discriminant features into which the data of the input pattern are classified; and
a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant features,
the feature selector comprising:
(a) a sample-data extractor extracting part of the samples as training samples and the remaining samples as test samples, from the samples;
(b) a classification estimator estimating whether the test samples corresponding to test objects belong to the specific class based on the feature information on the training samples, the class label information on the training samples, and the feature information on the test samples, for respective feature subsets of any combination of the features, and determining the correctness of the estimation based on the class label information on the test samples; and
(c) a discriminant feature determiner determining the discriminant features based on the correctness of the estimation for each of feature subsets, wherein,
the classification estimator
(b-1) calculates a first conditional probability and a second conditional probability based on the number of the training samples belonging to each category of the respective features, the first conditional probability is a probability that data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples, (b-2) calculates a first posterior probability that the test sample corresponding to the test object belongs to the specific class based on the feature information on the test sample, a first prior probability of occurrence of the specific class and the first conditional probability, (b-3) calculates a second posterior probability that the test sample corresponding to the test object belongs to the non-specific class based on the feature information on the test sample, a second prior probability of occurrence of the non-specific class and the second conditional probability, (b-4) outputs classification information indicating a result of an estimation on whether the test samples corresponding to the test objects belong to the specific class by comparing the first posterior probability with the second posterior probability, and (b-5) outputs judgement information indicating the correctness of the estimation by comparing the classification information of the test samples with the class label information on the test samples, and the discriminant feature determiner (c-1) specifies the feature subsets corresponding to the judgement information satisfying a predetermined condition among the judgement information of the respective feature subsets, and (c-2) determines the features included in the specified feature subsets as the discriminant features.

12. The information processor according to claim 11, wherein the classification estimator calculates the first prior probability and the second prior probability.

13. The information processor according to claim 11, wherein,
the sample-data extractor extracts the test samples from the samples,
the classification estimator outputs the judgement information for each of the test samples, and
the discriminant feature determiner determines the discriminant features, based on the judgement information of each of the test samples.

14. The information processor according to claim 13, wherein, the classification estimator
calculates the first conditional probability, the second conditional probability, the first posterior probability and the second posterior probability and outputs the classification information, for each of the test samples, and
outputs the judgement information for each of the test samples, based on the classification information of each of the test samples.

15. The information processor according to claim 11, wherein the first prior probability is equal to the second prior probability.

16. A non-transitory computer readable medium encoded with a program for processing information instructing a computer to function as the information processor according to claim 11.

17. A method of processing information carried out by an information processor determining whether an input pattern corresponding to an input object belongs to a specific class among multiple classes, based on discriminant features selected from multiple features with a plurality of categories, the information processor comprising:
a feature selector selecting the discriminant features from the multiple features;
a classification determiner determining whether the input pattern corresponding to the input object belongs to the specific class based on the categories of the respective features into which data of the input pattern are classified; and
a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant features,
the method comprising:
(a) a sample-data extraction step of extracting part of the samples as training samples and the remaining samples as test samples, from the samples;
(b) a class estimation step of estimating whether the test samples corresponding to test objects belong to the specific class based on the feature information on the training samples, the class label information on the training samples, and the feature information on the test samples, for respective feature subsets of any combination of the features, and determining correctness of the estimation based on the class label information on the test samples; and
(c) a discriminant feature determination step of determining the discriminant features based on the determined result of the correctness of the estimation for each of feature subsets, wherein,
the class estimation step comprising:
(b-1) a step of calculating a first conditional probability and a second conditional probability based on the number of the training samples belonging to each category of the respective features, the first conditional probability is a probability that the data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples,
(b-2) a step of calculating the first posterior probability that the test sample corresponding to the test object belongs to the specific class based on the feature information on the test sample, the first prior probability of occurrence of the specific class and the first conditional probability,
(b-3) a step of calculating a second posterior probability that the test sample corresponding to the test object belongs to the non-specific class based on the feature information on the test sample, a second prior probability of occurrence of the non-specific class and the second conditional probability, (b-4) a step of outputting classification information indicating a result of an estimation on whether the test samples corresponding to the test objects belong to the specific class by comparing the first posterior probability with the second posterior probability, and (b-5) a step of outputting judgement information indicating the correctness of the estimation by comparing the classification information on the test samples with the class label information on the test samples, and the discriminant feature determination steps comprising:

(c-1) a step of specifying the feature subsets corresponding to the judgement information satisfying a predetermined condition among the judgement information of the respective feature subsets, and (c-2) a step of determining the features included in the specified feature subsets, as the discriminant features.

18. An information processor selecting a discriminant feature subset used for determining whether an input object belongs to a specific class among multiple classes, the information processor comprising:

a feature selector selecting the discriminant feature subset from multiple feature subsets of any combination of a plurality of features, each feature comprises multiple categories; and a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant feature subset, the feature selector comprising:

(a) a sample-data extractor extracting part of the samples as training samples and the remaining samples as test samples, from the samples;

(b) a classification estimator estimating whether the test samples corresponding to test objects belong to the specific class based on the feature information on the training samples, the class label information on the training samples, and the feature information on the test samples, for respective feature subsets, and determining the correctness of the estimation based on the class label information on the test samples; and (c) a discriminant feature determiner determining the discriminant feature subset based on the correctness of the estimation for each of feature subsets, wherein, the classification estimator (b-1) calculates a first conditional probability and a second conditional probability based on the number of the training samples belonging to each category of the respective features, the first conditional probability is a probability that the data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples, (b-2) calculates a first posterior probability that the test sample corresponding to the test object belongs to the specific class based on the feature information on the test sample, a first prior probability of occurrence of the specific class and the first conditional probability, (b-3) calculates a second posterior probability that the test sample corresponding to the test object belongs to the non-specific class based on the feature information on the test sample, a second prior probability of occurrence of the non-specific class and the second conditional probability, (b-4) outputs classification information indicating a result of an estimation on whether the test samples corresponding to the test objects belong to the specific class by comparing the first posterior probability with the second posterior probability, and (b-5) outputs judgement information indicating the correctness of the estimation by comparing the classification information of the test samples with the class label information on the test samples, and the discriminant feature determiner determines the feature subset as the discriminant feature subset, the feature subset corresponds to the judgement information satisfying a predetermined condition among the judgement information of the respective feature subsets.

19. The information processor according to claim 18, wherein the classification estimator calculates the first prior probability and the second prior probability.

20. The information processor according to claim 18, wherein the first prior probability is equal to the second prior probability.

21. The information processor according to claim 18, wherein, the sample-data extractor extracts the test samples from the samples, the classification estimator outputs the judgement information for each of the test samples, and the discriminant feature determiner determines the discriminant feature subsets based on the judgement information of each of the test samples.

22. The information processor according to claim 18, wherein, the classification estimator calculates the first conditional probability, the second conditional probability, the first posterior probability and the second posterior probability and outputs the classification information, for each of the test samples, and outputs the judgement information for each of the test samples, based on the classification information of each of the test samples.

23. A non-transitory computer readable medium encoded with a program for processing information instructing a computer to function as the information processor according to claim 18.

24. A method of processing information carried out by an information processor selecting a discriminant feature subset used for determining whether an input object belongs to a specific class among multiple classes, the information processor comprising:
- a feature selector selecting the discriminant feature subset from multiple feature subsets of any combination of a plurality of features, each feature comprises multiple categories; and
- a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant feature subset, the method comprising:
- (a) a sample-data extraction step of extracting part of the samples as training samples and the remaining samples as test samples, from the samples;
- (b) a classification estimation step of estimating whether the test samples corresponding to test objects belong to the specific class based on the feature information on the training samples, the class label information on the training samples, and the feature information on the test samples, for respective feature subsets, and determining the correctness of the estimation based on the class label information on the test samples; and
- (c) a discriminant feature determination step of determining the discriminant feature subset based on the correctness of the estimation for each of feature subsets, wherein, the classification estimation step comprising:
- (b-1) a step of calculating a first conditional probability and a second conditional probability based on the number of the training samples belonging to each category of the respective features, the first conditional probability is a probability that the data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples,
- (b-2) a step of calculating a first posterior probability that the test sample corresponding to the test object belongs to the specific class based on the feature information on the test sample, a first prior probability of occurrence of the specific class and the first conditional probability,
- (b-3) a step of calculating a second posterior probability that the test sample corresponding to the test object belongs to the non-specific class based on the feature information on the test sample, a second prior probability of occurrence of the non-specific class and the second conditional probability,
- (b-4) a step of outputting classification information indicating a result of an estimation on whether the test samples corresponding to the test objects belong to the specific class by comparing the first posterior probability with the second posterior probability, and
- (b-5) a step of outputting judgement information indicating the correctness of the estimation by comparing the classification information of the test samples with the class label information on the test samples, and the discriminant feature determination step comprising:
- a step of determining the feature subset as the discriminant feature subset, the feature subset corresponds to the judgement information satisfying a predetermined condition among the judgement information of the respective feature subsets.

25. An information processor determining whether an input object belongs to a specific class among multiple classes, based on discriminant feature subset consisted of a plurality of discriminant features, each discriminant feature comprises multiple categories, the information processor comprising:
- a storage storing an input pattern corresponding to the input object, a first conditional probability and a second conditional probability, the first conditional probability is a probability that the data of the input pattern belong to categories corresponding to the respective discriminant features for the specific class, the second conditional probability is a probability that the data of the input pattern belong to categories corresponding to the respective discriminant features for a non-specific class which is a class other than the specific class among classes; and
- a classification determiner determining whether the input object belongs to the specific class based on the categories of the respective discriminant features into which data of the input pattern are classified, wherein
- the input pattern is associated with feature information indicating the categories of the respective discriminant features into which the data of the input pattern are classified, and
- the classification determiner
- calculates a first posterior probability that the input object belongs to the specific class based on the feature information on the input pattern, a first prior probability of occurrence of the specific class and the first conditional probability,
- calculates a second posterior probability that the input object belongs to the non-specific class based on the feature information on the input pattern, a second prior probability of occurrence of the non-specific class and the second conditional probability, and
- determines whether the input object belongs to the specific class by comparing the first posterior probability with the second posterior probability.

26. The information processor according to claim 25, wherein the discriminant feature subset is selected from feature subsets of any combination of a plurality of features by a same or different information processor configured for selecting a discriminant feature subset used for determining whether an input object belongs to a specific class among multiple classes, the same or different information processor comprising:
- a feature selector selecting the discriminant feature subset from multiple feature subsets of any combination of a plurality of features, each feature comprises multiple categories; and
- a storage storing feature information indicating the categories of the respective features into which the data of samples are classified and class label information indicating whether the samples corresponding to sample objects belong to the specific class, the feature information and the class label information being provided for the samples corresponding to the respective sample objects used for selection of the discriminant feature subset, the feature selector comprising:
(a) a sample-data extractor extracting part of the samples as training samples and the remaining samples as test samples, from the samples;
(b) a classification estimator estimating whether the test samples corresponding to test objects belong to the specific class based on the feature information on the training samples, the class label information on the training samples, and the feature information on the test samples, for respective feature subsets, and determining the correctness of the estimation based on the class label information on the test samples; and
(c) a discriminant feature determiner determining the discriminant feature subset based on the correctness of the estimation for each of feature subsets, wherein, the classification estimator
(b-1) calculates a first conditional probability and a second conditional probability based on the number of the training samples belonging to each category of the respective features, the first conditional probability is a probability that the data of the input pattern belong to categories corresponding to the respective features included in the feature subsets for the specific class, the second conditional probability is a probability that the data of the input pattern belong to categories corresponding to the respective features included in the feature subsets for a non-specific class which is a class other than the specific class among classes, and the number of the training samples is counted for each class based on the feature information on the training samples and the class label information on the training samples,
(b-2) calculates a first posterior probability that the test sample corresponding to the test object belongs to the specific class based on the feature information on the test sample, a first prior probability of occurrence of the specific class and the first conditional probability,
(b-3) calculates a second posterior probability that the test sample corresponding to the test object belongs to the non-specific class based on the feature information on the test sample, a second prior probability of occurrence of the non-specific class and the second conditional probability,
(b-4) outputs classification information indicating a result of an estimation on whether the test samples corresponding to the test objects belong to the specific class by comparing the first posterior probability with the second posterior probability, and
(b-5) outputs judgement information indicating the correctness of the estimation by comparing the classification information of the test samples with the class label information on the test samples, and the discriminant feature determiner determines the feature subset as the discriminant feature subset, the feature subset corresponds to the judgement information satisfying a predetermined condition among the judgement information of the respective feature subsets.

27. A non-transitory computer readable medium encoded with a program for processing information instructing a computer to function as the information processor according to claim 26.

28. A method of processing information carried out by an information processor determining whether an input object belongs to a specific class among multiple classes, based on discriminant feature subset consisted of a plurality of discriminant features, each discriminant feature comprises multiple categories, the information processor comprising:

a storage storing an input pattern corresponding to the input object, a first conditional probability and a second conditional probability, the first conditional probability is a probability that the data of the input pattern belong to categories corresponding to the respective discriminant features for the specific class, the second conditional probability is a probability that the data of the input pattern belong to categories corresponding to the respective discriminant features for a non-specific class which is a class other than the specific class among classes; and a classification determiner determining whether the input object belongs to the specific class based on the categories of the respective discriminant features into which data of the input pattern are classified, wherein the input pattern is associated with feature information indicating the categories of the respective discriminant features into which the data of the input pattern are classified, the method comprising:

a step of calculating a first posterior probability that the input object belongs to the specific class based on the feature information on the input pattern, a first prior probability of occurrence of the specific class and the first conditional probability;

a step of calculating a second posterior probability that the input object belongs to the non-specific class based on the feature information on the input pattern, a second prior probability of occurrence of the non-specific class and the second conditional probability; and a step of determining whether the input object belongs to the specific class by comparing the first posterior probability with the second posterior probability.

* * * * *